US010406189B2

(12) United States Patent
Johnson

(10) Patent No.: US 10,406,189 B2
(45) Date of Patent: *Sep. 10, 2019

(54) METHODS AND COMPOSITIONS FOR TREATING AND PREVENTING SIGNS OR SYMPTOMS OF EYE DISEASE

(71) Applicant: Johnson Living Trust dated October 26, 2001, Leonidas A. Johnson, Trustee, Diamond Bar, CA (US)

(72) Inventor: Leonidas A. Johnson, Diamond Bar, CA (US)

(73) Assignee: Leonidas A. Johnson, Diamond Bar, CA (US); Johnson Living Trust dated Oct. 23, 2001

( * ) Notice: Subject to any disclaimer, the term of this patent is extended or adjusted under 35 U.S.C. 154(b) by 0 days.

This patent is subject to a terminal disclaimer.

(21) Appl. No.: 14/994,469

(22) Filed: Jan. 13, 2016

(65) Prior Publication Data

US 2016/0120924 A1 May 5, 2016

Related U.S. Application Data

(63) Continuation of application No. 14/304,808, filed on Jun. 13, 2014, now Pat. No. 9,265,809.

(60) Provisional application No. 61/889,343, filed on Oct. 10, 2013, provisional application No. 61/888,871, filed on Oct. 9, 2013.

(51) Int. Cl.

| | | |
|---|---|---|
| *A61K 36/00* | (2006.01) | |
| *A61K 36/28* | (2006.01) | |
| *A61K 31/616* | (2006.01) | |
| *A61K 31/416* | (2006.01) | |
| *A61K 45/06* | (2006.01) | |
| *A61K 31/352* | (2006.01) | |
| *A61K 31/417* | (2006.01) | |
| *A61K 9/00* | (2006.01) | |
| *A61K 9/08* | (2006.01) | |
| *A61K 31/4172* | (2006.01) | |
| *A61K 36/185* | (2006.01) | |

(52) U.S. Cl.
CPC ............ *A61K 36/28* (2013.01); *A61K 9/0048* (2013.01); *A61K 9/0051* (2013.01); *A61K 9/08* (2013.01); *A61K 31/352* (2013.01); *A61K 31/416* (2013.01); *A61K 31/417* (2013.01); *A61K 31/4172* (2013.01); *A61K 31/616* (2013.01); *A61K 36/185* (2013.01); *A61K 45/06* (2013.01)

(58) Field of Classification Search
CPC .................................................... A61K 36/00
USPC ....................................................... 424/725
See application file for complete search history.

(56) References Cited

U.S. PATENT DOCUMENTS

| | | | | |
|---|---|---|---|---|
| 4,370,324 | A | * | 1/1983 | Bernstein ............... A61K 31/00 514/217 |
| 7,776,364 | B2 | * | 8/2010 | Thierman ............ A61K 31/185 424/717 |
| 7,795,203 | B2 | | 9/2010 | Babizhayev |
| 2003/0017216 | A1 | | 1/2003 | Schmidt et al. |
| 2007/0060639 | A1 | | 3/2007 | Wermeling |
| 2007/0275098 | A1 | | 11/2007 | Banks |
| 2008/0033027 | A1 | | 2/2008 | Bascomb et al. |
| 2009/0215852 | A1 | | 8/2009 | Bascomb et al. |
| 2010/0222587 | A1 | | 9/2010 | Hughes et al. |
| 2012/0165299 | A1 | | 6/2012 | Sharma |
| 2012/0142652 | A1 | | 9/2012 | Hughes et al. |

FOREIGN PATENT DOCUMENTS

| | | | | |
|---|---|---|---|---|
| CN | 001762350 | A | * | 4/2006 |
| EP | 1417970 | | * | 5/2004 |
| EP | 1417970 | B1 | | 12/2004 |
| EP | 2216026 | A1 | | 11/2010 |
| WO | 2008075149 | A2 | | 6/2008 |

OTHER PUBLICATIONS

Adams, R. et al., "Senecio Alkaloids: The Isolation of Senecionine from Senecio Cineraria and Some Observations on the Structure of Senecionine" Isolation and Structure of Senecionine, Journal of American Chemistry Society, Jun. 1949; vol. 71; pp. 1953-1956.
Anitha TS, et al., "Prevention of selenite-induced cataractogenesis by an ethanolic extract of Cineraria maritima: an experimental evaluation of the traditional eye medication" Journal Biological Trace, Oct. 2011, vol. 143, No. 1, pp. 425-436.
Atherton, Ken, "Practice and Principles in making Fresh Plant Tinctures" Pindari Herb Farm, Dec. 2009, http://www.pindariherbfarm.com/educate/fpt.htm.
Abraham, T. Girgih, et al., "Reverse-phase HPLC Separation of Hemp Seed (*Canabis sativa* L.) Protein Hydrolysate Produced Peptide Fractions with enhanced Antioxidant Capacity", Journal of Plant Foods for Human Nutrition, Feb. 16, 2013, vol. 68, pp. 39-46.
"Optique 1 Eye Drops—BOIRON USA—Homeopathic Medicines" BOIRON, Screen capture Sep. 27, 2013, www.boironusa.com/products/optique-eyedrops/.
Robson, Philip, "Therapeutic aspects of cannabis and cannabinoids" Journal of the British Journal of Psychiatry, 2001, vol. 178, pp. 107-115.
"Cineraria Maritima Schwabe Eye Drops Prevent Cataract", Ebay, Screenshot Sep. 9, 2013, http://www.ebay.com/itm/Cineraria-Maritima-Schwabe-Eye-Drops-Prevent-Cataract-non-alcoholic-lot-of-two-/300684466408.
Shi, Qiong, et al. "Effect of a combination of carnosine and aspirin eye drops on streptozotocin induced diabetic cataract in rats", Journal of National Center for Biotechnology Information, Oct. 21, 2009, vol. 15, pp. 2129-2138, http://www.ncbi.nlm.nih.gov/pmc/articles/PMC2773744/.

(Continued)

*Primary Examiner* — Michael V Meller
(74) *Attorney, Agent, or Firm* — Fish IP Law, LLP

(57) ABSTRACT

Compositions and methods for the treatment and prevention of at least one of a sign and a symptom associated with an eye disease are disclosed. Preferred compositions could comprise a liquid formulation including *Cineraria maritima* and at least one of a nonsteroidal anti-inflammatory drug, a carnosine, and a cannabinoid.

1 Claim, 1 Drawing Sheet

(56) References Cited

OTHER PUBLICATIONS

"Allergy Eye Relief Homeopathic sterile eye drops", Screenshot Sep. 27, 2013, www.similasanusa.com/allergy-eye-relief.
Toh, Tze'Yo, et al. "MEdical treatment of cataract", Journal of Clinical and Experimental Opthamology, 2007, vol. 35, pp. 664-671.
Kondrot, Edward, "Alternative Treatment of Cataracts", Screenshot Sep. 9, 2013, http://www.healingtheeye.com/Articles/Cataracts.html.
Kondrot, Edward, "Cataract Eye Drops with Cineraria" Screenshot Sep. 9, 2013, http://www.healingtheeye.com/products-cineraria-maritima.html.

* cited by examiner

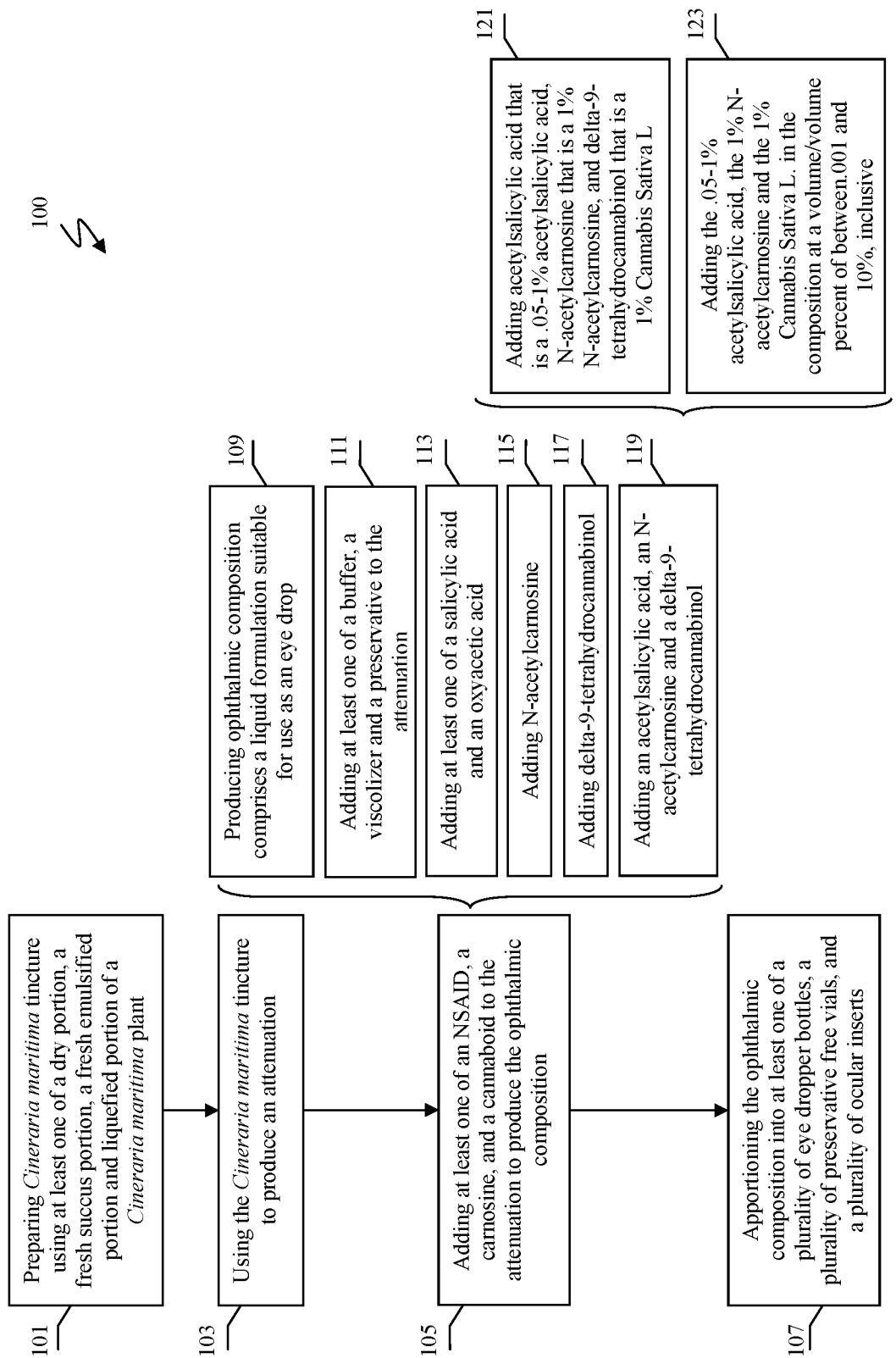

METHODS AND COMPOSITIONS FOR TREATING AND PREVENTING SIGNS OR SYMPTOMS OF EYE DISEASE

This application is a continuation of U.S. patent application Ser. No. 14/304,808, filed on Jun. 13, 2014, which claims the benefit of priority to co-pending U.S. provisional application having Ser. No. 61/888,871, filed on Oct. 9, 2013, and to co-pending U.S. provisional application having Ser. No. 61/889,343, filed on Oct. 10, 2013. These and all other publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is treatment and prevention of signs or symptoms of eye diseases, and more specifically treatment and prevention of signs or symptoms associated with cataracts.

BACKGROUND

The background description includes information that may be useful in understanding the present invention. It is not an admission that any of the information provided herein is prior art or relevant to the presently claimed invention, or that any publication specifically or implicitly referenced is prior art.

It is generally believed (by non-proponents of alternative medicine) that the only effective treatment for cataracts is surgery. While cataract surgery is considered to be generally safe, it can be a very daunting prospect for many individuals. Moreover, there are numerous risks associated therewith, including infection, swelling, bleeding, retinal detachment and loss of vision.

On the other side of the spectrum, homeopathic efforts have been put forth towards non-surgical alternatives to cataract surgery. Such efforts include eye drops having homeopathic active ingredients that are micro-diluted and homeopathically potentized.

Examples of known efforts can be found in U.S. Patent Application Publication Nos. 2003/0017216 to Schmidt et al., 2007/0275098 to Banks, 2008/0033027 to Bascomb et al., 2008/0033027 to Bascomb et al., 2009/0215852 to Bascomb et al., 2010/0222587 to Hughes et al., and 2012/0142652 to Hughes et al.

Unfortunately, there is apparently a clear divide between proponents of mainstream conventional medicine and proponents of homeopathic alternatives. While some proponents of mainstream medicine have attempted to find alternatives to cataracts eye surgery, they have apparently failed to consider the possible use of homeopathic ingredients or preparations. See, for example, Shi, qiong et al (Oct. 21, 2009) Effect of a Combination of Carnosine and Aspirin Eye Drops on Streptozotocin-Induced Diabetic Cataracts in Rats. Mol Vis. 2009; 15: 2129-2138 (Oct. 21, 2009), see http://www.ncbi.nlm.nih.gov/pmc/articles/PMC2773744. Therefore, people have failed to appreciate that superior compositions and methods could be achieved using a combination of homeopathic remedies and allopathic medicine.

Thus, there is still a need for compositions and methods of treating and preventing signs or symptoms associated with eye diseases.

SUMMARY OF THE INVENTION

The inventive subject matter provides apparatus, systems and methods in which compositions (e.g., liquid formulations, ophthalmic compositions, ocular inserts, etc.) comprising a *Cineraria maritima* component (herbal/homeopathic) combined with one of more of a nonsteroidal inflammatory drug (NSAID), a carnosine and a cannabinoid (e.g., an extract, a purified extract, etc.). In some embodiments, the liquid formulation could be formulated as an eye drop.

In some preferred embodiments, the *Cineraria maritima* will be present in the liquid formulation with a potency of no less than 12×. However, all suitable potencies of *Cineraria maritima* are contemplated, including for example, 1×, between 1× and 2×, inclusive, between 2× and 6×, inclusive, no less than 8×, no less than 6×, between 2× and 14×, inclusive or even at least 26×, at least 30×, or higher. Some formulations could be prepared homeopathically via dynamisation or potentisation. It should be appreciated that the *Cineraria maritima* component could be prepared with other ingredients (e.g., NSAID, carnosine, cannabinoid, etc.), or could be prepared separately and other ingredients later added. Thus, it is contemplated that at least one of an NSAID, a carnosine or a cannabinoid could be added to a 2× (or other attenuation) of *Cineraria maritima*. In such embodiments, the *Cineraria maritima* attenuation could comprise any suitable volume % of the final liquid formulation, including for example, at least 1 vol %, at least 10 vol %, at least 15 vol %, at least 25 vol %, at least 35 vol %, at least 45 vol %, at least 50 vol %, at least 65 vol %, at least 75 vol %, at least 85 vol %, at least 90 vol %, or even at least 95 vol % or more. The balance could comprise one or more pharmaceutically active and inactive ingredients.

In some aspects of the inventive subject matter, the NSAID could comprise a salicylic acid, such as acetylsalicylic acid, or an oxyacetic acid (e.g., Bendazac, etc.), and the cannabinoid could be delta-9-tetrahydrocannabinol. It should be appreciated that other active or inactive ingredients could be included in a liquid formulation of the inventive subject matter, including for example, an alcohol such as a glycol (e.g., polyethylene glycol, polypropylene glycol, propylene glycol, etc.), an semisynthetic ophthalmic lubricant (e.g., hypromellose, etc.), an acid (e.g., boric acid, phosphonic acid, etc.), or any other suitable ingredients.

Thus, it should be appreciated that a composition of the inventive subject matter could comprise, among other combinations, *Cineraria maritima* and an NSAID; *Cineraria maritima* and a carnosine; *Cineraria maritima* and a cannabinoid; *Cineraria maritima*, NSAID and carnosine; *Cineraria maritima*, NSAID and cannabinoid; *Cineraria maritima*, carnosine and cannabinoid; *Cineraria maritima*, NSAID, cannabinoid and carnosine; cannabinoid and an NSAID; cannabinoid and carnosine; or any combinations thereof.

Viewed from another perspective, the inventive subject matter also provides a method of producing an ophthalmic composition for treatment or prevention of a sign of symptom of an ophthalmic disease. Contemplated methods comprise of preparing a *Cineraria maritima* tincture using at least one of a dry portion, a fresh succus portion, a fresh emulsified portion, and a liquefied portion of a *Cineraria maritima* plant. In some preferred embodiments, the *Ciner-*

*aria maritima* tincture could be prepared using at least two, at least three, or even all portions of a *Cineraria maritima* plant. The *Cineraria maritima* tincture is used to produce an attenuation having a potency between 2× and 14×. At least one of an NSAID, a carnosine, and a cannabinoid could be added to the attenuation to produce the ophthalmic composition. In typical embodiments, the ophthalmic composition can be apportioned into at least one of a plurality of eye dropper bottles, a plurality of preservative free vials, and a plurality of ocular inserts.

In another aspect, the inventive subject matter also provides a method of treating or preventing at least one sign or symptom associated with cataracts or other eye disorder or disease. For example, a method (or composition) of the inventive subject matter could be used to prevent or treat both a symptom (e.g., decrease in clarity of vision, etc.) and a sign (e.g., grey or white pupil, etc.) associated with cataracts. Other signs and symptoms can include an indication of decreased visual acuity, decreased contrast sensitivity, distorted color vision, increased glare sensitivity, blurry vision, cloudy vision, hazy vision, a dimming of vision, or sensitivity to bright light. Contemplated methods for treating or preventing signs or symptoms associated with cataracts comprises a step of preparing a composition having *Cineraria maritima* and at least one of an NSAID, a carnosine and a cannabinoid. Contemplated compositions can preferably be produced as an anterior eye drop solution. It should be noted that preparing the composition could comprise one or more sub-steps, including for example, dynamisation or potentisation of the *Cineraria maritima*, alone or with other active ingredients. Additionally or alternatively, contemplated methods could comprise a step of apportioning the composition in a plurality of eye dropper bottles for consumption.

Viewed from yet another perspective, the inventive subject matter also provides a method of manufacturing an eye drop solution containing a *Cineraria maritima* component. Contemplated methods could comprise a step of producing a liquid formulation that contains *Cineraria maritima* in a homeopathic amount or concentration, wherein the liquid formulation could comprise at least one of an NSAID, a carnosine and a cannabinoid in a non-homeopathic amount. Additionally or alternatively, the liquid formulation can be packaged as an eye drop for treating or preventing at least one sign or symptom associated with cataracts (e.g., a clouding in vision, a blurring in vision, a dimming in vision, a sensitivity to light, etc.), and could have a potency suitable for one or more of a prescription only formulation and a over the counter formulation.

In another aspect of the inventive subject matter, compositions and methods are provided in which a cannabinoid (e.g., Delta-9-tetrahydrocannabinol, etc.) is included in a liquid formulation for use in preventing or treating a sign or symptom associated with cataracts. It should be appreciated that the cannibinoid could be present as a sole active ingredient, or could be combined with one or more other active ingredients.

Various objects, features, aspects and advantages of the inventive subject matter will become more apparent from the following detailed description of preferred embodiments, along with the accompanying drawing FIGURES in which like numerals represent like components.

BRIEF DESCRIPTION OF THE DRAWING

FIG. 1 is a schematic view of an embodiment of producing an ophthalmic composition for treating an ophthalmic disease.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The present inventive subject matter is generally directed towards ophthalmic formulations comprising *Cineraria maritima*, and at least one of an NSAID, a carnosine and a cannabinoid in therapeutically effective concentrations for the treatment and prevention of ophthalmic diseases. More preferably, the ophthalmic formulations are produced in therapeutically effective concentrations for the treatment or prevention of a sign or symptom related to cataracts.

In typical embodiments, a composition suitable for treatment or prevention of an ophthalmic disease can be produced using a *Cineraria maritima* tincture attenuation having a potency of between 2× and 14×, inclusive, and at least one of a carnosine, a cannabinoid and an NSAID. The composition can be produced as a liquid formulation (e.g., liquid, gel, or ointment suspended in a fluid) suitable for use as an eye drop, or can comprise an ocular insert suitable for placement in an eye of a user. Additionally or alternatively, compositions according to the inventive subject matter may be administered using various routes, including orally (e.g., via capsules, tablets, aqueous suspensions, or solutions, etc.), parenterally, by inhalation, topically, rectally, nasally, or via an implanted reservoir, wherein the term "parenteral" as used herein includes subcutaneous, intravenous, intramuscular, intraarticular, intrasynovial, intrathecal, intrahepatic, intralesional, and intracranial administration (typically injection or infusion).

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

In some aspects of the inventive subject matter, contemplated formulations could include a pharmacologically acceptable derivate of *Cineraria maritima*, preferably as an extract, and more preferably a homeopathically diluted tincture, at a potency of no greater than 1× attenuation. As used herein, a potency of no greater than 1× includes potencies of 2×, 4×, 8× ... nX, wherein 1× refers to a mother tincture which is a mix of one part of the crude botanical material and approximately nine parts of menstruum (alcohol, distilled water, or a combination of both). As used herein, the term "approximately" means within 20%. For example, approximately nine parts means between 7.2 parts to 10.8 parts, inclusive (e.g., exactly 9 parts or exactly 10 parts, etc.). Where *Cineraria maritima* is described as being present with a potency of 2×, one part of the 1× mother tincture of *Cineraria maritima* is mixed (optionally succussing) with approximately nine parts of water, alcohol or a combination thereof to create a 2× attenuation. Similarly, subsequent attenuations are prepared by mixing (optionally succussing) one part of the preceding attenuation with approximately nine parts of diluents. For example, where *Cineraria maritima* is described as being present with a potency of 6×, the mother tincture is mixed with approximately nine parts of water, alcohol or a combination thereof to result in a 2× preparation, the 2× preparation is mixed with approximately nine parts of water or alcohol to result in a 3× preparation, the 3× preparation is mixed with approximately nine parts of water or alcohol to result in a 4× preparation, the 4× preparation is mixed with approximately nine parts of water or alcohol to result in a 5× preparation, and the 5× preparation is mixed with approximately nine parts of water or alcohol to result in a 6× preparation. In some embodiments, the water, alcohol or combination thereof (the menstruum) comprises a HPUS approved diluent, and the step of mixing an attenuation with a diluent comprises succussion (vigorous shaking). It is contemplated that preparation of the attenuation involves vigorously shaking (succussed) to distribute the *Cineraria maritima* thoroughly. This vigorous shaking could be performed after each time a dilution is made, after some of the dilutions are made, or could be skipped.

It should also be appreciated that *Cineraria maritima* could be present in compositions of the inventive subject matter in any suitable amount or concentration, and could comprise a non-homeopathic preparation. Some possible methods that could be used to prepare an extract of *Cineraria maritima* (e.g., leaves, stems, seeds, etc.), which could be combined with other active and inactive ingredients, comprise drying parts (e.g., aerial or underground parts, etc.) of *Cineraria maritima* plants, grinding the plant into a powder (coarse or fine, etc.), and then extracting the powder with ethanol or other solvent, for example, using a Soxhlet apparatus. Any suitable amount of the powder (e.g., approximately 1 g, approximately 5 g, approximately 10 g, approximately 25 g, between 1-5 g, between 4-8 g, between 4-6 g, between 5-10 g, etc.) could be extracted with any suitable volume of the diluents (e.g., approximately 50 mL, approximately 75 mL, approximately 100 mL, approximately 150 mL, approximately 200 mL, approximately 500 mL, between 50-150 mL, between 100-150 mL, etc.). The resulting product could optionally be concentrated to a dry mass by vacuum distillation. An exemplary method of preparing extracts of *Cineraria maritima* can be found in Anitha T S, Annadurai T, Thomas, P A et al (Oct. 14, 2010) Prevention of Selenite-Induced Cataractogenesis by an Ethanolic Extract of *Cineraria maritima*: An Experimental Evaluation of the Traditional Eye Medication. Biol Trace Elem Res (2011) 143:425-436.

Thus, any suitable portions of any suitable amount of *Cineraria maritima* could be extracted using any suitable volume of any suitable diluent in any suitable manner.

Most typically, contemplated compositions will comprise at least one other active ingredient. It is contemplated that a synergistic effect could arise when at least one other active ingredient is combined with *Cineraria maritima* (e.g., *Cineraria maritima* and an NSAID, *Cineraria maritima* and carnosine, *Cineraria maritima* and a cannabinoid, etc.). For example, it is contemplated that a combination of *Cineraria maritima* with at least one other ingredient could be at least 5%, at least 10%, at least 25%, at least 50%, or even at least 100% or more effective to treating or preventing a sign or symptom associated with cataracts than the combined total effect of the two or more ingredients used separately. It should also be appreciated that a synergistic effect could arise when two or more active ingredients are combined (e.g., an NSAID and carnosine, an NSAID and cannabinoid, carnosine and cannabinoid, etc.).

Among contemplated ingredients (active or inactive) for the composition are nonsteroidal anti-inflammatory drugs (or NSAID). In one embodiment, the composition comprises *Cineraria maritima* and an NSAID, and the NSAID is at least one of a salicylic acid and an oxyacetic acid. Other examples of NSAID that can be used include salicylates, propionic acid derivatives, acetic acid derivatives, enolic acid derivatives, fenamic acid derivatives, coxibs, sulphonanilides, etc. In some preferred embodiments, the NSAID can be acetylsalicylic acid or Bendazac.

Additionally, or alternatively, among contemplated ingredients (active or inactive) for the composition are cannibinoids. In one embodiment, the composition comprises *Cineraria maritima* and a cannibinoid, and the cannabinoid is delta-9-tetrahydrocannabinol. However, other examples of cannibinoids that can be used include cannabigerol, cannabichromene, cannabicycol, cannabivarin, tetrahydrocannabino (e.g., Delta-9-Tetrahydrocannabinol, etc.), cannabidivarin, cannabichromevarin, cannabigerovarin, cannabigerol monomethyl ether, etc.

Additionally, or alternatively, among contemplated ingredients (active or inactive) for the composition are carnosines (e.g., N-acetylcarnosine, etc.). In one embodiment, the composition comprises *Cineraria maritima* and a carnosine, and the carnosine is N-acetylcarnosine.

Each of the active ingredients (e.g., *Cineraria maritima*, delta-9-tetrahydrocannabinol, acetyl salicylic acid, ocyacetic acid, bendazac, carnosine, etc.) could be present in an eye drop, ocular inserts or other formulation in any suitable amount, including for example, less than 0.00001%, less than 0.001%, at least 0.01%, at least 0.05%, between 0.01-0.05%, at least 0.1%, at least 0.2%, between 0-0.2%, at least 0.25%, between 0.00001-0.25%, at least 0.3%, at least 0.4%, at least 0.5%, between 0.3-0.5%, at least 1%, between 0-1%, at least 2%, between 0-2%, between 1-2%, at least 2.5%, at least 5%, between 1-5%, at least 10%, between 5-10%, at least 25%, between 15-25%, at least 50%, between 25-50%, between 50-60%, or even 90% or more. In general and unless the context dictates otherwise, all concentrations herein should be interpreted as follows: (1) wt/wt % for solid ingredients; (2) wt/vol % for a solid in a liquid; and (3) vol/vol % for liquid ingredients. Such concentrations could advantageously be effective to prevent or relieve at least one sign or symptom associated with at least one of the following eye disorders: (a) cataracts (e.g., cloudy or blurred vision, decrease in visual acuity, sensitivity to light or glare, decreased contrast sensitivity, poor night vision, dimming, altered color vision, grey or white pupil, etc.); (b) diabetic retinopathy (e.g., blurred vision, loss of vision, macular edema, floaters, retinal and vitreous hemorrhages, exudates, etc.); (c) glaucoma (e.g., blurred vision and decreased visual acuity, loss of peripheral vision, visual field defect, optic nerve damage, high inter ocular pressure (TOP), retinal fiber defect, etc.); (d) macular degeneration (e.g., blurred vision, decreased visual acuity, distortion of straight lines, distortion in central vision, macular edema, macular drusen, maculopathy, etc.); (e) dry eye syndrome (e.g., irritated eyes, sandy or gritty sensation, red eyes, burning sensation, poor visual acuity, poor tear quality, decreased tear break up time, poor schrimer test performance, increased eye sensitivity to wind and heat, etc.); (f) proptosis (e.g., dryness, eye pain, eye redness, etc.); (g) keratoconus (e.g., distorted vision, ghost images, sensitivity to light, eye strain, etc.); (h) pterygium/pinguecula (e.g., distorted vision, blurred vision, decreased visual acuity, inflammation, irregular astigmatism, etc.); (i) ocular allergy (e.g., eye irritation, blurred vision, decreased visual acuity, etc.; or any other eye disorders and signs or symptoms.

Furthermore, it is contemplated that the composition comprises more than one active ingredient. For example, the composition can comprise Cineraria maritima, carsonine, and a cannibinoid or Cineraria maritima, carsonine, and an NSAID or Cineraria maritima, an NSAID, and a cannibinoid or Cineraria maritima, a carnosine, a cannabinoid and an NSAID. In some embodiments, the Cineraria maritima can have a potency in the composition of between 2×-12×, inclusive, and the composition further comprises an acetylsalicylic acid, a N-acetylcarnosine and a delta-9-tetrahydrocannabinol. As discussed above, the amount of active ingredients can vary in the composition. For example, it is contemplated that in some compositions, the acetylsalicylic acid could be a 0.05-1% acetylsalicylic acid, the N-acetylcarnosine could be a 1% N-acetylcarnosine, and the delta-9-tetrahydrocannabinol could be a 1% Cannabis Sativa L.

It should be apparent that the total concentration of active ingredients within the composition can also vary. For example, 0.05-1% acetylsalicylic acid, 1% N-acetylcarnosine and 1% Cannabis Sativa L. can be present in the composition at a volume/volume percent (vol/vol %) of between 0.0001 and 10%, inclusive. More generally, the total concentration of active ingredients (carnosine, a cannabinoid and an NSAID) with respect to the overall composition can be controlled to therapeutically effective concentrations for the treatment or prevention of a sign or symptom related to cataracts.

In some embodiments, a composition of the inventive subject matter could additionally or alternatively comprise a lubricant (e.g., glycerin, polysorbate, hypromellose, hydroxyethyl cellulose, carboxymethylcellulose, etc.), a redness reliever (e.g., naphazoline hydrochloride, tetrahydrozoline, etc.), an astringent (e.g., zinc sulfate, etc.) or various inactive ingredients (e.g., borate buffer, silver sulphate preservative, benzalkonium chloride, boric acid, chlorobutanol, edentate disodium, menthol, sodium borate, calcium chloride, magnesium chloride, potassium chloride, sodium chloride, sodium lactate, a pH adjuster (e.g., hydrochloric acid, sodium hydroxide, etc.), a buffer, etc.).

Also contemplated are, among other things, homeopathic ingredients such as Belladonna, Euphrasia, Hepar sulphyris, Apis, or Sabadilla, each of which can be present in homeopathic dilutions, including for example, at least 1×, at least 2×, at least 6×, at least 8×, at least 12×, or even at least 26× or more.

It should be appreciated that each active ingredient (e.g., Cineraria maritima, carnosine, NSAID, cannabinoid, etc.) could be prepared using any suitable method. Some suitable methods could be found in, among other things, (1) Das S et al. Protein Based Nanoparticles as Platforms for Aspirin Delivery for Ophthalmologic Applications. Colloids and Surfaces B: Biointerfaces 93 (2012) 161-168; (2) Adams R et al. (1949) Senecio Alkaloids: The Isolation of Senecionine From Senecio Cineraria and Some Observations on the Structure of Senecionine. J Am Chem Soc 1949; 71; 1953-1956; and (3) Girgih A T et al. Reserve-phase HPLC Separation of Hemp Seed (Cannabis sativa L.) Protein Hydrolysate Produced Peptide Fractions with Enhanced Antioxidant Capacity. Plant Foods Hum Nutr (2013) 68: 39-46.

In another aspect, the inventor has discovered a method of producing an ophthalmic composition for treatment or prevention of a sign of symptom of an ophthalmic disease. To illustrate, FIG. 1 shows a schematic demonstrating an exemplary method 100 of producing an ophthalmic composition. As shown in step 101, a Cineraria maritima tincture can be prepared using at least one of a dry portion, a fresh succus portion, a fresh emulsified portion and a liquefied portion of a Cineraria maritima plant.

Contemplated methods can include using a single portion of the Cineraria maritima plant to produce the Cineraria maritima tincture, such as using only one of the dry portion, the fresh succus portion, the fresh emulsified portion and the liquefied portion. In other contemplated embodiments, more than one portion of the Cineraria maritima plant can be used to produce the Cineraria maritima tincture. For example, a combination of a dry portion and a fresh succus portion, a dry portion and a fresh emulsified portion, a dry portion and a liquefied portion, a fresh succus portion and a fresh emulsified portion, a fresh succus portion and a liquefied portion, a dry portion, a fresh succus portion, and a fresh emulsified portion, all portions of Cineraria maritima plant, and all other combinations thereof can be suitable to prepare the Cineraria maritima tincture.

Tinctures are typically prepared by maceration or percolation from crude botanical substances (e.g., Cineraria maritima plant), fresh or dried, by the dissolving action of an alcoholic vehicle. Contemplated embodiments of preparing a Cineraria maritima tincture include an alcohol menstruum (e.g., ethanol). The alcohol menstruum can be of various concentrations. For example, the alcohol menstruum can be a designated strength as standardized by the Homoeopathic Pharmacopoeia of the United States (HPUS) (e.g., 65%) or any other concentration suitable to produce a Cineraria maritima tincture.

It should be apparent that a Cineraria maritima tincture can be produced having various volumes. The volume of the Cineraria maritima tincture can be influenced by, among other things, at least one of (i) the quantity of Cineraria maritima plant to macerate/pulverize/emulsify/liquefy and (ii) the quantity of Cineraria maritima tincture required to be produced.

Different tinctures can be produced by the methods disclosed herein. For example, it is contemplated that a Class C Tincture can be produced having one part by weight of dry crude material in ten parts by weight of completed solution. As a more specific example, a Cineraria maritima tincture can be produced having a strength of 1:10 being 1 part (dry weight) of Cineraria maritima into 10 parts of menstruum in accordance to the standards made by HPUS for Cineraria maritima.

As shown in step 103, the Cineraria maritima tincture can be used to produce an attenuation having a potency of no greater than 1×, for example, a potency of between 2× and 14×, inclusive. As explained above, a mother tincture (e.g., fresh plant tincture, Cineraria maritima tincture) can contain approximately 1/10 (0.10±20%) part of the dry crude substance, and therefore corresponds to the 1× attenuation. One milliliter (1.0 ml) of the mother tincture can be succussed with nine milliliters (9.0 ml) of diluent to produce ten milliliters (10.0 ml) of a 2× attenuation. Subsequent attenuations can be prepared by succussing 1.0 ml of the preceding attenuation with 9.0 ml (or approximately 9 ml) of diluent to produce 10.0 ml of the succeeding attenuation. It is contemplated that the diluent solution is at least one of purified water and active and inactive ingredients.

As shown in step 105, one or more of an NSAID, a carnosine, and a cannabinoid can be added to the attenuation to produce the ophthalmic composition. The ophthalmic composition can be a liquid formulation (e.g., gel, liquid, suspended ointment) suitable for use as an eye drop as shown in step 109 or the ophthalmic composition can be produced as an ocular insert, among other things. As described above, it is contemplated that one, two or all three of the NSAID, the carnosine, and the cannabinoid can be added to the attenuation to produce the ophthalmic composition. Contemplated embodiments include all combinations of the NSAID, the carnosine, and the cannabinoid (e.g., NSAID and cannibinoid, NSAID and carnosine, carnosine and cannabinoid, etc.).

Various types of NSAIDs, carnosines, and cannabinoids can be added to the attenuation to produce the ophthalmic composition. For example, step 113 shows that at least one of a salicylic acid (e.g., acetylsalicylic acid) and an oxyacetic acid can be added to the attenuation. In another example, step 115 shows that N-acetylcarnosine can be added to the attenuation. In yet another example, step 117 shows that delta-9-tetrahydrocannabinol can be added to the attenuation. While discussed separately, it is contemplated that acetylsalicylic acid, N-acetylcarnosine and delta-9-tetrahydrocannabinol can all be added or combinations thereof (e.g., acetylsalicylic acid and N-acetylcarnosine, acetylcarnosine and delta-9-tetrahydrocannabinol, etc.) can be added to the attenuation. Such components can comprise, among other things, 0.05-1% acetylsalicylic acid, 1% N-acetylcarnosine, and 1% *Cannabis Sativa* L. as shown in step 121. Furthermore, each of the 0.05-1% acetylsalicylic acid, the 1% N-acetylcarnosine and the 1% *Cannabis Sativa* L. can be present in the ophthalmic composition at a weight/volume percent (wt/vol %) of between 0.001 and 10%, inclusive as shown in step 123.

Ingredients besides those considered active (e.g., inactive ingredients) can also be added to the attenuation. For example, inactive ingredients comprising at least one of a buffer, a viscolizer and a preservative can be added to the attenuation as shown in step 111. Buffers can include pre-buffers, such as sterile water, sodium chloride, potassium chloride, and isotonic sodium borate solution (e.g., 2.6% solution). Buffers can also include biological buffer solutions, such as Cyclohexylaminopropanesulfonic Acid (e.g., 0.2M solution) and TrisHydroxypropylMethylaminopropanesulfonic Acid (e.g., 0.2M solution). Suitable viscolizers comprise Carboxymethylcellulose sodium, Hydroxypropylmethylcellulose (e.g., 0.7% solution), and Guar gum (e.g., 0.375% solution). Suitable preservatives include Preservative Free (PF) single use containers and Polysorbate 80 (preserving agent for bottle).

Additionally, alkaline water/solutions can be used to hydrolyze proteins (e.g., hemp seed proteins). For example, contemplated agents include sodium hydroxide and potassium hydroxide.

It should be appreciated that various combinations of inactive ingredients can be added to the attenuation. For example, it is contemplated that a buffer and viscolizer, buffer and preservative, viscolizer and preservative, and all three can be added to the attenuation. Thus, it is evident that numerous combinations of inactive ingredients can be paired with numerous combinations of active ingredients as discussed above and added to the attenuation to produce various ophthalmic compositions.

Once the ophthalmic composition is produced, step 107 shows that the ophthalmic composition can be apportioned into, among other things, a plurality of eye dropper bottles, a plurality of preservative free vials, or a plurality of ocular inserts. The ocular inserts can be low concentration, implanted and slow release.

To better illustrate some of the compositions and methods described herein, an example is provided. It should be noted that the example and data provided herein is not intended to, and should not be interpreted as limiting the scope of the inventive subject matter.

In an illustrative example, a *Cineraria maritima* tincture can be produced having 1:10 strength being 1 part by weight of *Cineraria maritima* into 10 parts of menstruum. The menstruum can be an approximately 65% (i.e., 63-67%, inclusive) alcohol menstruum or any other suitable menstruum (e.g., approximately 35%, approximately 45%, approximately 55%, approximately 75%, approximately 85%, approximately 95%, between 45-95%, inclusive, between 45-75%, inclusive, between 75-95%, inclusive, between 75-85%, inclusive, etc.). In contemplated embodiments, the *Cineraria maritima* tincture can be produced to fill a 5000 milliliter (ml) volume. The amount of *Cineraria maritima* pulverized/emulsified/liquefied can be approximately 500 grams, preferably 460 grams, and most preferably 450 grams of dry weight (or 450 ml liquid volume). Moreover, the amount of 100% alcohol menstruum to produce 65% alcohol menstruum can be approximately 3000 ml, preferably 2960 ml, and most preferably 2950 ml. By way of example, a *Cineraria maritima* tincture having an attenuation of 1× can be produced to fill a 5,000 ml volume using about 450 grams of *Cineraria maritima*, about 2960 ml of 100% alcohol and about 1600 ml of water (it should be noted that the combination of water and alcohol produces about a 65% alcohol menstruum). The aerial parts of the *Cineraria maritima* plant (preferably before flowering) can be mixed (e.g., pulverized, emulsified, liquefied, etc.) with menstruum and at least one of (i) macerated (soaked) and (ii) percolated (simmered) for any suitable amount of time (e.g., 1 day-10 weeks, 1 week-7 weeks, 1 week-5 weeks, or more preferably approximately 3 weeks (e.g., 17-25 days).

Such production of tincture is preferably produced using a unique formula that calculates the weight of fresh (wet) *Cineraria maritima* to use by converting the dry weight FIGURE into a liquid volume. This is contrary to that apparently taught by the *Cineraria maritima* Fresh Plant Tincture Traditional Formula that calculates the weight of fresh (wet) *Cineraria maritima* by multiplying the dry weight formula by the inverted dry weight percentage, which is problematic because the fresh *Cineraria maritima* generally has too much water content to make fresh tincture the traditional way.

A mother tincture, such as a *Cineraria maritima* tincture, that contains approximately 1/10 (0.10±20%) part of the fresh crude botanical substance, corresponds to the 1× attenuation. However, the attenuation can be modified via successions. For example, a 2× attenuation can be produced by taking 1/10 unit of mother fresh plant tincture (e.g., *Cineraria maritima* tincture) and mixing the tincture with 9/10 units of diluent solution (e.g., purified water or other active and inactive ingredients). In another example, a 3× attenuation can be produced by taking 1/10 unit of 2× tincture and mixing the tincture with 9/10 units of solution (e.g., purified water or other active and inactive ingredients of finalized medication preparations).

Once the appropriate attenuation is produced, ophthalmic compositions can be produced using at least one of a carnosine, a cannabinoid and an NSAID. For example, an ophthalmic composition comprising a *Cineraria maritima*/acetylsalicylic acid (1%) solution can be produced. The *Cineraria maritima*/acetylsalicylic acid (1%) solution can comprise of *Cineraria maritima* tincture 2× succession, 10% acetylsalicylic acid (1%) solution, a viscolizer (0.1% Carboxymethylcellulose sodium), a biological buffer solution (0.2M cyclohexylaminopropanesulfonic acid), and Polysorbate 80 (preservative).

By way of example, a 10 ml ophthalmic composition having *Cineraria maritima*/acetylsalicylic acid (1%) can be produced using 1-3 ml (preferably 1 ml) from *Cineraria maritima* tincture 2× succession, 1-3 ml (preferably 1 ml) from acetylsalicylic acid (1%) solution, and at least one of 3-5 ml (preferably 4 ml) of viscolizer (preferably 0.1% Carboxymethylcellulose sodium), 3-5 ml (preferably 4 ml) of biological buffer solution (preferably 0.2M cyclohexylaminopropanesulfonic acid), and Polysorbate 80 (preservative). It is contemplated that the acetylsalicylic acid (1%) solution is produced by combining acetylsalicylic acid and Albumin (pure egg white powder) in strong alkaline (preferably pH 12) filtered water (NaOH+$H_2O$) with a high speed mixer.

In another example, an ophthalmic composition having *Cineraria maritima*/N-acetylcarnosine (1%) combination can be produced. By way of example, a 10 ml volume of the composition having *Cineraria maritima*/N-acetylcarnosine (1%) combination can comprise 1-3 ml (preferably 1 ml) *Cineraria maritima* tincture 2× succession, 1-3 ml (preferably 1 ml) from 10% N-acetylcarnosine solution, and at least one of 3-5 ml (preferable 4 ml) viscolizer (preferably 0.1% Carboxymethylcellulose sodium), 3-5 ml (preferably 4 ml) of biological buffer solution (preferably 0.2M cyclohexylaminopropanesulfonic acid) and Polysorbate 80. The 10% N-acetylcarnosine solution can be produced by combining N-acetylcarnosine powder in filtered water and mixing with a high speed mixer.

In another example, an ophthalmic composition having *Cineraria maritima*/D-9 hemp solution (1%) can be produced. As used herein, delta-9-tetrahydrocannabinol (D-9) refers to Hemp Seed (*Cannabis sativa* L.) protein peptide fractions. By way of example, a 10 ml volume of the composition having *Cineraria maritima*/D-9 hemp solution (1%) can comprise 1-3 ml (preferably 1 ml) *Cineraria maritima* tincture 2× succession, 1-3 ml (preferably 1 ml) from 10% D-9 hemp solution, and at least one of 3-5 ml (preferable 4 ml) viscolizer (preferably 0.1% Carboxymethylcellulose sodium), 3-5 ml (preferably 4 ml) of biological buffer solution (preferably 0.2M cyclohexylaminopropanesulfonic acid) and Polysorbate 80. The 10% D-9 Hemp solution can be produced by combining hemp seed protein powder in strong alkaline (preferably pH 12) filtered water (NaOH and/or KOH) and mixing with high speed mixer.

In another example, an ophthalmic composition having *Cineraria maritima*/acetylsalicylic acid (0.05-1%)/n-acetylcarnosine (1%)/D-9 hemp (1%) can be produced. By way of example, a 10 ml volume of the composition having *Cineraria maritima*/acetylsalicylic acid (0.05-1%)/n-acetylcarnosine (1%)/D-9 hemp (1%) can comprise 1-3 ml (preferably 1 ml) *Cineraria maritima* tincture 2× succession, 1-3 ml (preferably 1 ml) from acetylsalicylic acid (1%) solution, 1-3 ml (preferably 1 ml) from 10% N-acetylcarnosine solution, 1-3 ml (preferably 1 ml) from 10% D-9 hemp solution, and at least one of 3-5 ml (preferable 4 ml) viscolizer (preferably 0.1% Carboxymethylcellulose sodium), 1-5 ml (preferably 2 ml) of biological buffer solution (preferably 0.2M cyclohexylaminopropanesulfonic acid) and Polysorbate 80.

While a portion of the above disclosure is directed towards liquid formulations suitable for use as eye drops, it should be appreciated that the compositions disclosed herein having *Cineraria maritima* and the at least one other active ingredient could be formulated in any suitable dosage form for any suitable route of administration. Suitable dosage forms include, among other things, ocular inserts, tablets, capsules, thin film, liquid solution or suspension, powder, pellets, pastes, cream, gel, transdermal patch, or parenteral (e.g., suitable for infusion, injection or implantation). Contemplated liquid formulations include liquid form (e.g., eye drops), a gel, and a suspended ointment. Contemplated ocular inserts include low concentration, implanted, and slow release inserts. Moreover, the ocular inserts can be biodegradable or non-biodegradable. It is also contemplated that the formulations could be provided in single-use or multi-use containers.

Additionally, while the above disclosure is directed to *Cineraria maritima* and at least one of a carnosine, a cannabinoid and an NSAID, it is contemplated that a composition can comprise of solely *Cineraria maritima* in therapeutically effective concentrations for the treatment or prevention of a sign or symptom related to cataracts. By way of example, a 10 ml volume of an ophthalmic composition can be produced having *Cineraria maritima* comprising 1-3 ml (preferably 1 ml) from *Cineraria maritima* tincture 2× succession, and at least one of 3-5 ml (preferably 4 ml) of viscolizer (preferably 0.1% Carboxymethylcellulose sodium), 3-7 ml (preferably 5 ml) of biological buffer solution (preferably 0.2M cyclohexylaminopropanesulfonic acid), and Polysorbate 80 (preservative).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A composition for treatment of a cataract in a human in need thereof consisting essentially of:
    an alcohol extract of at least one of a dry portion, a fresh succus portion, a fresh emulsified portion, and a liquefied portion of *Cineraria maritima;*
    at least 1% N-acetylcarnosine;
    0.05% to 1% acetylsalicylic acid; and
    at least 1% *Cannabis Sativa* L.

* * * * *